(12) United States Patent
Bradwell et al.

(10) Patent No.: US 7,875,183 B2
(45) Date of Patent: Jan. 25, 2011

(54) METHOD OF REMOVING ANTIBODY FREE LIGHT CHAINS FROM BLOOD

(75) Inventors: Arthur Randell Bradwell, Birmingham (GB); Hermann Goehl, Bisingen-Zimmern (DE); Markus Storr, Filderstadt (DE)

(73) Assignees: Gambro Lundia AB (SE); The Binding Site Group Limited (GB)

( * ) Notice: Subject to any disclaimer, the term of this patent is extended or adjusted under 35 U.S.C. 154(b) by 199 days.

(21) Appl. No.: 11/599,849

(22) Filed: Nov. 15, 2006

(65) Prior Publication Data

US 2007/0251882 A1 Nov. 1, 2007

(30) Foreign Application Priority Data

Apr. 27, 2006 (GB) ................. 0608444.6

(51) Int. Cl.
| | |
|---|---|
| B01D 11/00 | (2006.01) |
| B01D 61/00 | (2006.01) |
| C02F 1/44 | (2006.01) |
| A61M 1/16 | (2006.01) |
| A61M 1/34 | (2006.01) |

(52) U.S. Cl. ............ 210/646; 210/500.27; 210/500.36; 210/651

(58) Field of Classification Search ................. 210/646, 210/656, 195.2, 321; 604/5, 6
See application file for complete search history.

(56) References Cited

U.S. PATENT DOCUMENTS

2004/0214761 A1* 10/2004 Raison et al. ................. 514/12
2006/0144782 A1* 7/2006 Buck ..................... 210/500.23

FOREIGN PATENT DOCUMENTS

| WO | WO02/49745 | * 6/2002 | ................. 210/646 |
|---|---|---|---|
| WO | 2004/056460 | 7/2004 | |
| WO | 2006/079816 | 8/2006 | |

OTHER PUBLICATIONS

High-Cut Off Protein Permeable Membrane, GAMBRO, retrieved from http://www.gambro.at/_rtf-gambro/CMS_fg475d6180139d7_orig_1512.pdf on Apr. 14, 2009.*
Conventional Chemotherapy Treatment for Mulitple Myeloma, Multiple Myeloma Research Foundation (MMRF) [retrieved from http://www.multiplemyeloma.org/treatments/3.02.php on Apr. 14, 2009].*

(Continued)

*Primary Examiner*—Krishnan S Menon
*Assistant Examiner*—Dirk Bass
(74) *Attorney, Agent, or Firm*—Barnes & Thornburg LLP

(57) ABSTRACT

There is provided a method of reducing blood free light chain concentration in a subject, the method comprising the step of subjecting the subject's blood to haemodialysis, haemodiafiltration or haemofiltration. There is also provided the use of a dialysis membrane which is a membrane that allows passage of molecules having a molecular weight of up to 45 kDa in presence of whole blood, and has a molecular weight exclusion limit in water of about 200 kDa in the preparation of a haemodialysis unit for conducting haemodialysis, haemodiafiltration or haemofiltration on a subject to reduce blood free light chain concentration in the patient.

17 Claims, 8 Drawing Sheets

OTHER PUBLICATIONS

Blade, J., "Management of renal, hematologic, and infectious complications", Myeloma: Biology and Management, 3rd edition, pp. 251-267.

Bradwell, A.R., "Diseases with increased polyclonal free light chains", Serum Free Light Chain Analysis, 2nd edition, Birmingham, UK, The Binding Site Ltd., pp. 145-151.

Bradwell et al., "Rapid removal of free light chains from Serum by hemodialysis for patients with myeloma kidney", Blood, the Journal of the American Society of Hematology, vol. 106, No. 11, Nov. 16, 2005, 1 page.

Bradwell et al., "Serum free light chain immunoassays and their clinical application", Clinical and Applied Immunology Reviews, vol. 3, No. 1-2, Nov. 2002, pp. 17-33.

Bradwell et al., "Diseases with increased polyclonal free light chains," Serum Free Light Chain Analysis, 3rd Edition, Birmingham, UK, The Binding Site Ltd., pp. 175-185.

Clark et al., "Plasma exchange when myeloma presents as acute renal failure: a randomized, controlled trial", Ann Intern Med., vol. 143, No. 11, 2005, pp. 777-784.

Clark et al., Haematologica/ the hematology journal, vol. 90, supplement No. 1, Apr. 2005, p. 117.

Cohen et al., "Effect of dialysis on serum/plasma levels of free immunoglobulin light chains in end-stage renal disease patients", Nephrology Dialysis Transplantation, vol. 17, 2002, pp. 879-883.

Johnson et al., "Treatment of renal failure associated with multiple myeloma—plasmapheresis, hemodialysis, and chemotherapy", Arch. Intern. Med., vol. 150, Apr. 1990, pp. 863-869.

Mead et al., "Serum free light chains for monitoring multiple myeloma", British Journal of Haematology, vol. 126, pp. 348-354.

Morgera et al., "High permeability haemofiltration improves peripheral blood mononuclear cell proliferation in septic patients with acute renal failure", Nephrol. Dial. Transplant vol. 18, 2003, pp. 2570-2576.

Morgera et al., "Intermittent high permeability hemofiltration in septic patients with acute renal failure", Intensive Care Med. vol. 29, 2003, 1989-1995.

Morgera et al., "Renal replacement therapy with high-cutoff hemofilters: impact of convection and diffusion on cytokine clearances and protein status", American Journal of Kidney Diseases, vol. 43, No. 3, Mar. 2004, pp. 444-453.

Naka et al., "Myoglobin clearance by super high-flux hemofiltration in a case of severe rhabdomyolysis: a case report", Critical Care, vol. 9 No. 2, Apr. 2005, pp. 90-95.

Nowrousian et al., "Serum free light chain analysis and urine immunofixation electrophoresis in patients with multiple myeloma", Clinical Cancer Res., vol. 11(24), Dec. 15, 2005, pp. 8706-8714.

Pratt et al., "The tumor kinetics of multiple myeloma following autologous stem cell transplantation as assessed by measuring serum-free light chains," Leukemia and Lymphoma, vol. 47(1), Jan. 2006, pp. 21-28.

Ritz, E., "Cast nephropathy in myeloma—does PACAP38, a new member of the vasoactive intestinal peptide family, open a therapeutic window?", Journal of the American Society of Nephrology, 2006, pp. 911-913.

Russo et al., "Renal handling of albumin: a critical review of basic concepts and perspective", American Journal of Kidney Diseases, vol. 39, No. 5, May 2002, pp. 899-919.

Sanders et al., "Pathobiology of cast nephropathy from human Bence Jones proteins", J. Clin. Invest, vol. 89, Feb. 1992, pp. 630-639.

Solomon A., "Light chains of human immunoglobulins" Methods in Enzymology, vol. 116, 1985, pp. 101-121.

Tauro et al., "Recovery of renal function after autologous stem cell transplantation in myeloma patients with end-stage renal failure", Bone Marrow Transplantation, vol. 30, 2002, pp. 471-473.

Ward R.A., "Protein-leaking membranes for hemodialysis: a new class of membranes in search of an application?" Journal of the American Society of Nephrology, vol. 16, 2005, pp. 2421-2430.

Winearls C.G., "Acute myeloma kidney", Kidney International, vol. 48, 1995, pp. 1347-1361.

Winearls C.G., "Myeloma kidney", Comprehensive Clinical Nephrology, 2nd edition, Johnson & Feehally, Harcourt Publishers, chapter 17, pp. 235-241.

Ying et al., "Mapping the binding domain of immunoglobulin light chains for Tamm-Horsfall protein", American Journal of Pathology, vol. 158, No. 5, May 2001, pp. 1859-1866.

Zuccelli et al., "Controlled plasma exchange trial in acute renal failure due to multiple myeloma", Kidney International, vol. 33, 1988, pp. 1175-1180.

Hutchison et al., "Efficient removal of immunoglobulin free light chains by hemodialysis for multiple myeloma: in vitro and in vivo studies," Journal of the American Society of Nephrology, vol. 18, 2007, pp. 886-895.

Drueke, T.B., "Beta2-microglobulin and amyloidosis," Nephrology Dialysis Transplantation: Official Publication of the European Dialysis and transplant Association -European Renal Association, vol. 15, Suppl. 1, (2000), pp. 17-24.

Machiguchi et al, "Efficacy of haemodiafiltration treatment with PEPA dialysis membranes in plasma free light chain removal in a patient with primary amyloidosis," Nephrology Dialysis Transplantation, vol. 17, Sep. 2002, pp. 1689-1691.

* cited by examiner

METHOD OF REMOVING ANTIBODY FREE LIGHT CHAINS FROM BLOOD

CROSS REFERENCE TO RELATED APPLICATION

This application claims the benefit under 35 U.S.C. §119 (a) of GB Application Serial No. 0608444.6, filed Apr. 27, 2006, the disclosure of which is incorporated herein by reference.

TECHNICAL FIELD

The present invention relates to the field of removing free light chains from blood, particularly methods for such removal and apparatus for use in such methods.

BACKGROUND OF THE INVENTION

Antibody molecules (also known as immunoglobulins) have a twofold symmetry and are composed of two identical heavy chains and two identical light chains, each containing variable and constant domains. The variable domains of the heavy and light chains combine to form an antigen-binding site, so that both chains contribute to the antigen-binding specificity of the antibody molecule. The basic tetrameric structure of antibodies comprises two heavy chains covalently linked by a disulphide bond. Each heavy chain is in turn attached to a light chain, again via a disulphide bond, to produce a substantially "Y"-shaped molecule.

There are two types of light chain: Lambda ($\lambda$) and Kappa ($\kappa$). There are approximately twice as many $\kappa$ as $\lambda$ molecules produced in humans, but this is quite different in some mammals. Each chain contains approximately 220 amino acids in a single polypeptide chain that is folded into one constant and one variable domain. Plasma cells produce one of the five heavy chain types together with either $\kappa$ or $\lambda$ molecules. There is normally approximately 40% excess free light chain production over heavy chain synthesis. Where the light chain molecules are not bound to heavy chain molecules, they are known as "free light chain molecules" (FLCs). The $\kappa$ light chains are usually found as monomers. The $\lambda$ light chains tend to form dimers.

There are a number of proliferative diseases associated with antibody producing cells. FIG. 1 shows the development of B-cell lineage and associated diseases. These diseases are known as malignant B-cell diseases. They are summarised in detail in the book "Serum-free Light Chain Analysis" A. R. Bradwell, available from The Binding Site Limited, Birmingham, UK (ISBN: 07044 24894), Third Edition 2005, and the Second Edition of the book (2004, ISBN 07044 24541).

In many such diseases a plasma cell proliferates to form a monoclonal tumour of identical plasma cells. This results in production of large amounts of identical immunoglobulins and is known as monoclonal gammopathy.

Diseases such as myeloma and primary systemic amyloidosis (AL amyloidosis) account for approximately 1.5% and 0.3% respectively of cancer deaths in the United Kingdom. Multiple myeloma (MM) is the second-most common form of haematological malignancy after non-Hodgkin lymphoma. In Caucasian populations the incidence is approximately 40 per million per year. Conventionally, the diagnosis of MM is based on the presence of excess monoclonal plasma cells in the bone marrow, monoclonal immunoglobulins in the serum or urine and related organ or tissue impairment such as hypercalcaemia, renal insufficiency, anaemia or bone lesions. Normal plasma cell content of the bone marrow is about 1%, while in MM the content is typically greater than 30%, but may be over 90%.

AL amyloidosis is a protein conformation disorder characterised by the accumulation of monoclonal free light chain fragments as amyloid deposits. Typically, these patients present with heart or renal failure but peripheral nerves and other organs may also be involved.

The Binding Site Ltd have previously developed a sensitive assay that can detect the free $\kappa$ light chains and, separately, the free $\lambda$ light chains (PCT/GB2006/000267, published as WO2006/079816). This method uses a polyclonal antibody directed towards either the free $\kappa$ or the free $\lambda$ light chains. The detection of free light chains (FLC) is discussed in detail in the book by A. R. Bradwell. The possibility of raising such antibodies was also discussed as one of a number of different possible specificities, in WO97/17372. This form of assay has been found to successfully detect free light chain concentrations. Furthermore, the sensitivity of the technique is very high.

Bradwell A. R., et al. (Clin. & Applied Immunol. Reviews 3 (2002), 17-33) reviews serum free light chain immunoassays and their applications. Historically, urine concentrations of FLC have not been considered to accurately reflect plasma cell synthesis. Hence, there has been a move away from testing urine concentrations to serum-based FLC assays, using techniques such as nephelometry and immunofixation electrophoresis. The paper summarises the understanding in the art of FLC synthesis and metabolism with respect to renal function.

Approximately 12-20% of MM patients first present in acute renal failure. 10% are dialysis dependent in the long term.

Free $\kappa$ and free $\lambda$ are cleared by filtration through the kidneys and the rate depends on their molecular size. Monomeric free light chains, characteristically K, are cleared in 2-4 hours at 40% of the glomerular filtration rate. Dimeric free light chains, typically $\lambda$, are cleared in 3-6 hours at 20% of the glomerular filtration rate, while large molecules are cleared more slowly. Removal may be prolonged to 2-3 days in MM patients in renal failure, when serum free light chains (sFLCs) are removed by the liver and other tissues (Russo et al. (2002) Am. J. Kidney Dis. 39 899-919). In contrast, IgG has a half-life of 21 days that is not affected by renal impairment.

There are approximately 0.5 million nephrons in each human kidney. Each nephron contains a glomerulus with pores that allow filtration of serum molecules into its proximal tubule. The pore sizes are variable with a restriction in filtration commencing at about 40 kDa and being almost complete by 65 kDa. Protein molecules that pass the glomerular pores are then either absorbed unchanged or degraded in the proximal tubular cells and excreted as fragments. This is an essential mechanism to prevent loss of proteins and peptides into the urine and is very efficient. The exact pathway of free light chain is unknown but between 10-30 g per day can be processed by the kidneys, so, under normal conditions, very little free light chain passes beyond the proximal tubules.

After filtration by the glomeruli, FLCs enter the proximal tubules and bind to brush-border membranes via low-affinity, high-capacity receptors called cubulins (gp280) (Winearls (2003) "Myeloma Kidney"—Ch. 17 Comprehensive Clinical Nephrology, $2^{nd}$ Ed. Eds Johnson & Feehally; Pub: Mosby). Binding provokes internalisation of the FLCs and subsequent metabolism. The concentration of the FLCs leaving the proximal tubules, therefore, depends upon the amounts in the glomerular filtrate, competition for binding uptake from other proteins and the absorptive capacity of the tubular cells. A reduction in the glomerular filtration rate increases serum FLC concentrations so that more is filtered by the remaining functioning nephrons. Subsequently, and with increasing renal failure, hyperfiltering glomeruli leak albumin and other proteins which compete with FLCs for absorption, thereby causing more to enter the distal tubules.

FLCs entering the distal tubule normally bind to uromucoid (Tamm-Horsfall protein). This is the dominant protein in normal urine and is though to be important in preventing ascending urinary infections. It is a glycoprotein (85 kDa)

that aggregates into high molecular weight polymers of 20-30 units. Interestingly, it contains a short peptide motif that has a high affinity for FLCs (Ying & Sanders (2001) Am. J. Path. 158 1859-1866). Together, the two proteins form waxy casts that are more characteristically found in acute renal failure associated with light chain MM (LCMM) (see e.g. Winearls (1995) Kidney Int. 48 1347-1361). The casts obstruct tubular fluid flow, leading to disruption of the basement membrane and interstitial damage. Rising concentrations of sFLCs are filtered by the remaining functioning nephrons leading to a vicious cycle of accelerating renal damage with further increases in sFLCs. This may explain why MM patients, without apparent pre-existing renal impairment, suddenly develop renal injury and renal failure. The process is aggravated by other factors such as dehydration, diuretics, hypercalcaemia, infections and nephrotoxic drugs.

Serum FLC concentrations are abnormal in >95% of patients with MM and have a wide range of concentrations, but their inherent toxicity also varies considerably, as was shown by Sanders & Brooker using isolated rat nephrons (Sanders & Brooker (1992) J. Clin. Invest. 89 630-639). The toxicity is in part related to binding with Tamm-Horsfall protein (see e.g. Winearls (1995) Kidney Int. 48 1347-1361).

In spite of much effort to show otherwise, particular molecular charge and/or κ or λ type are not now considered relevant to FLC toxicity. Furthermore, highly polymerised FLCs (a frequent finding in MM) are probably not nephrotoxic because they cannot readily pass through the glomeruli. This may partly account for the lack of renal damage in some patients who have very high sFLC concentrations.

The amount of sFLCs necessary to cause renal impairment was recently studied by Nowrousain et al. (Clin. Cancer Res. (2005) 11 8706-8714), who showed that the median serum concentrations associated with overflow proteinuria (and hence potential for tubular damage) was 113 mg/L for κ and 278 mg/L for λ. These concentrations are approximately 5-to 10-fold above the normal serum concentrations and presumably relate to the maximum tubular reabsorption capacity of the proximal tubules. Since the normal daily production of FLC is ~500 mg, increases in ~5 g/day are likely to be nephrotoxic in many patients.

There have been several urine studies that have related urine FLC excretion rates to renal impairment. Typically, the associated renal impairment rises with increasing urine FLCs. One study showed that 5%, 17% and 39% of patients had renal impairment with excretion rates of <0.005 g/day, 0.005-2 g/day and >2 g/day, respectively (Blade (2003) "Management of Renal, Hematologic and Infectious Complications" in: Myeloma: Biology and Management, $3^{rd}$ Ed. Eds Malpas et al.; Pub: Saunders). However, FLC excretion is an indicator of renal damage in addition to its cause.

The pre-renal load of FLCs is an important factor in renal toxicity. In an attempt to minimise renal damage, plasma exchange (PE) has been used to reduce the pre-renal load of serum free light chains. Zuchelli et al. (Kidney Int. (1988) 33 1175-1180) compared MM patients on peritoneal dialysis (control group) with plasma exchange (and haemodialysis in some patients). Only 2 of 14 in the control group had improved renal function, compared with 13 of 15 in the plasma exchange arm. Survival was also improved (P<0.01).

This early success was not repeated in subsequent controlled trials. Johnson et al. (Arch Intern. Med. (1990) 150 863-869) compared 10 patients on forced diuresis with 11 who had additional plasma exchange and found no difference in outcome. Most recently, a large series was reported by Clarke et al. (Haematologica (2005) 90 (s1) 117; Kidney Int., Mar. 2006). Half of 97 patients who were on chemotherapy, haemodialysis or a combination of the two were randomly allocated to receive plasma exchange. Again, there was no statistically significant benefit from plasma exchange.

A subsequent editorial in JASN noted a number of shortcomings in plasma exchange studies, indicating that the efficiency of plasma exchange could not be judged (Ritz E., J. Am. Soc. Nephrol (2006), 17: 914-916).

BRIEF SUMMARY OF THE INVENTION

The applicants postulated that removal of serum free light chains by haemodialysis might be a way of reducing renal failure in patients with multiple myeloma (Bradwell et al. (2005) Blood 106 (11) 3482: 972a; $47^{th}$ Annual Meeting of American Society of Hematology, 10-13 Dec. 2005). The applicants have surprisingly found that a patient having excess serum free light chains can be treated by dialysis, with the result that free light chain concentration is reduced.

Conventional dialysers have a molecular weight cut-off around 15-20 kDa so the filtration efficiency for FLCs is very low. However, some new "protein leaking" dialysers have much larger pores (Ward (2005) J. Am. Soc. Nephrol. 16 2421-2430). These membranes were developed to provide higher clearances of low molecular weight proteins than do conventional high-flux dialysis membranes. A routine use for such membranes was not identified, since specific uremic toxins that are removed by protein-leaking membranes but not conventional high-flux membranes had not been identified. It was not clear whether the protein-leaking membranes offered benefits beyond those obtained with conventional high-flux membranes.

A new group of membranes used in intensive care, so called high cut-off (HCO) dialysers have been used within clinical studies to eliminate circulating sepsis-associated inflammatory mediators more effectively than with conventional dialysis membranes. These high cut-off membranes have much higher pore size than the other two groups mentioned above—the standard high flux dialyser membrane and the slightly protein permeable membrane. Pore sizes of the high cut-off membrane are in the range of 20 to 40 nm that means by a factor 3 bigger than the membranes with protein permeability and a factor of 4 larger than the standard high flux membranes. Definition of high cut-off membrane: cut-off for high cut-off membrane: molecular weight proteins which pass the membrane to less than 10%. High cut-off membranes have a molecular weight cut-off measured in blood or human plasma of 45000 Dalton whereas cut-off of a standard high flux membrane is in the range of 15000 Dalton and of a slightly protein permeable membrane in the range of 20000 Dalton. This cut-off measured in blood clearly indicates that molecular weight substances like FLC proteins the molecular weight from 20000 to 45000 can penetrate only high cut-off membranes in a significant amount.

Morgera, et al. show a remarkable clearance of interleukin-6 with high cut-off treatments leading to a significant decrease in circulating IL-6 levels in septic patients having acute renal failure (Morgera, et al. Intensive Care Med. (2003), 29: 1989-1995). Furthermore, the treatment lead to a restoration of immuneresponsiveness of blood cells in those patients (Morgera S., et al., Nephrol. Dial. Transplant (2003), 18: 2570-2576). A study where patients were randomly allocated to high cut-off CVVH or high cut-off CVVHD showed that convention and diffusion did not exhibit the expected difference in terms of clearance of middle-molecular-weight proteins, whereas using diffusion instead of convention significantly reduces the loss of albumin while maintaining good cytokine clearance rates. In CVVHD mode a maximum albumin loss of 950 mg per hour in patients treated with the HCO membrane was reported (Morgera S., et al. Am. J. Kidney Dis. (2004), 43: 444-453). The applicants have now surprisingly found that such membranes can be used to effectively reduce sFLC concentrations.

DETAILED DESCRIPTION

Figure 1:
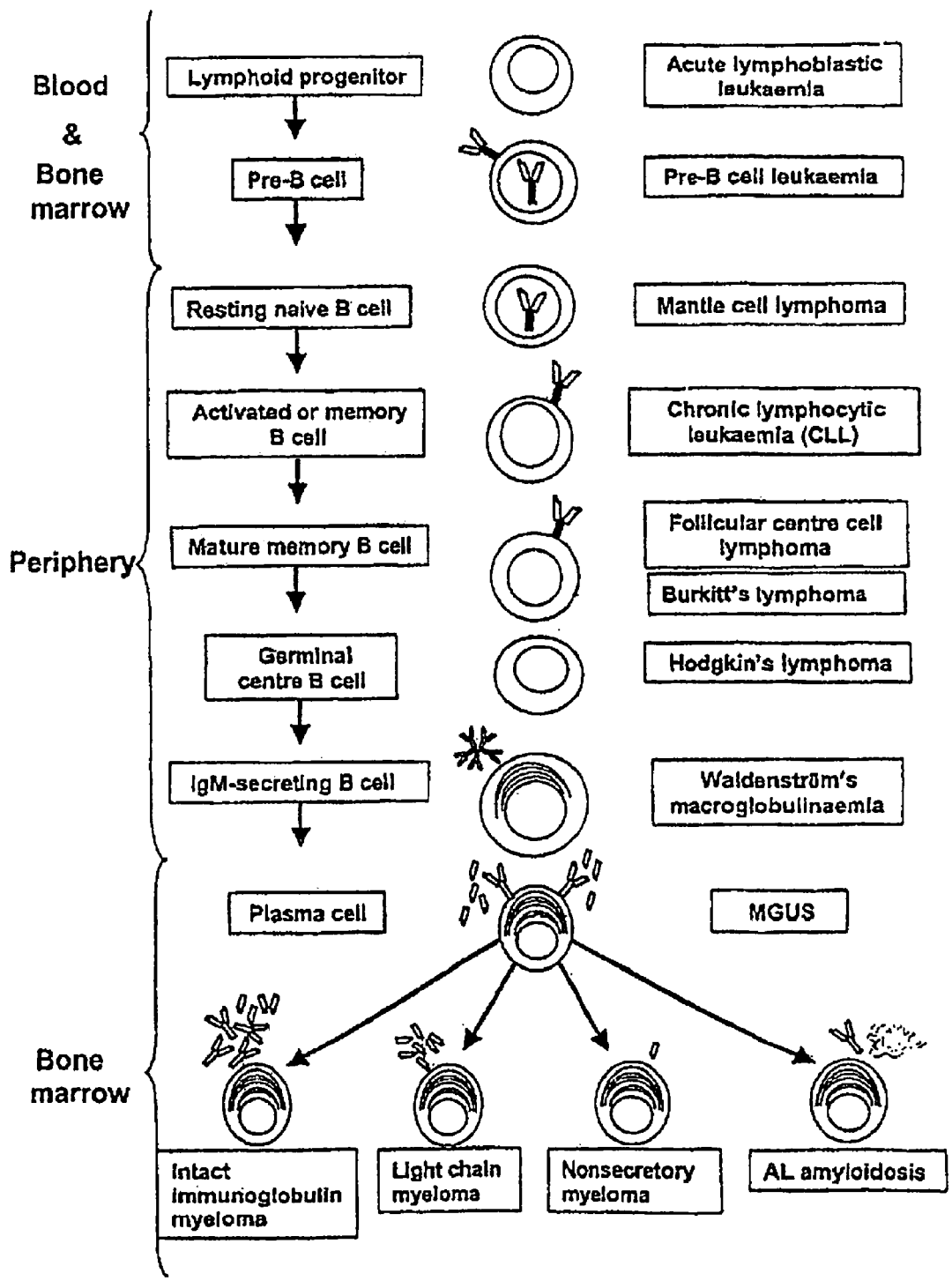
FIG. 1 shows proliferative diseases which are associated with antibody producing cells.

According to a first aspect of the invention, there is provided a method of reducing blood free light chain concentration in a subject, the method comprising the step of subjecting the subject's blood to haemodialysis, haemodiafiltration or haemofiltration.

Advantageously, the use of this method allows the effective removal of free light chains from the blood serum of a subject, with the result that the pre-renal FLC load is reduced and, therefore, that renal failure is prevented or slowed.

The subject may be a mammal and is preferably a human subject.

Preferably the dialysis membrane is a "super flux", "perm selective" or "protein leaking" membrane.

In a preferred embodiment, the haemodialysis, haemodiafiltration or haemofiltration step is carried out using a dialysis membrane which is a "protein-leaking" membrane, preferably using a high cut-off dialysis membrane which has a molecular weight cut-off greater than about 45 kDa, measured in blood or blood plasma. A protein-leaking membrane is preferably one which shows a permeability of serum albumin (molecular weight 67 kDa) of less than 0.1%, whereas the high cut-off membrane has a serum albumin permeability of less than 1%. Albumin permeability data is discussed in Ward RA. "Protein-leaking membranes for hemodialysis: a new class of membranes in search of an application?", J Am Soc Nephrol. 2005 Aug.; 16(8):2421-30 which is hereby incorporated by the reference.

The membrane is most preferably λ or κ free light chain leaking. That is, the λ or κ free light chains pass through the membrane. High flux membranes, with smaller pore sizes, have been observed to remove some free light chains. However, this appears to be primarily due to binding of the FLC onto the dialysis membranes.

Typically, protein-leaking and high cut-off membranes have a water permeability of >40 ml/h per mmHg/m in vitro. They may have a $\beta_2$-microglobulin clearance of at least 80 ml/min. for conventional hemodialysis with a blood flow rate of 300-400 ml/min. Albumin loss is preferably less than 2-6 g per 4 hours of dialysis. The sieving coefficient may be 0.9 to 1.0 for $\beta_2$-microglobulin and 0.01 to 0.03 for albumin.

Most preferably the membrane is a permselective membrane of the type disclosed in WO 2004/056460, incorporated herein by reference. Such membranes preferably allow passage of molecules having a molecular weight of up to 45,000 Daltons in the presence of whole blood and have a molecular weight exclusion limit in water of about 200,000 Daltons. The membrane is preferably in the form of a permselective asymmetric hollow fibre membrane. It preferably comprises at least one hydrophobic polymer and at least one hydrophilic polymer. Preferably the polymers are present as domains on the surface.

Such a membrane may be a hollow fiber having at least a 3-layer asymmetric structure with a separation layer present in the innermost layer of the hollow fiber. Preferably the separation layer has pores in the range of 15-60 nm, most preferably 20-40 nm. By, comparison: the standard high flux dialysis membrane has about 9 nm pore size and the slightly protein permeable membrane about 12 nm pore size.

The sieving coefficient for IL-6 in the presence of whole blood is preferably 0.9 to 1.0. Preferably the sieving coefficient for albumin in the presence of whole blood is below 0.05.

The hydrophobic polymer according to the invention may be chosen from the group consisting of polyarylethersulfone (PAES), polypropylene (PP), polysulfone (PSU), polymethylmethacrylate (PMMA), polycarbonate (PC), polyacrylonitrile (PAN), polyamide (PA), or polytetrafluorethylene (PTFE).

The hydrophilic polymer of the invention may be chosen from the group consisting of polyvinylpyrrolidone (PVP), polyethyleneglycol (PEG), polyvinylalcohol (PVA), and copolymer of polypropyleneoxide and polyethyleneoxide (PPO-PEO).

As used herein, the term "sieving coefficient (S)" refers to the physical property of a membrane to exclude or pass molecules of a specific molecular weight.

The sieving coefficient can be calculated according to standard EN 1283, 1996.

Put simply, the sieving coefficient of a membrane is determined by pumping a protein solution (bovine or human plasma) under defined conditions (QB, TMP and filtration rate) through a membrane bundle and determining the concentration of the protein in the feed, in the retentate and in the filtrate. If the concentration of the protein in the filtrate is zero, a sieving coefficient of 0% is obtained. If the concentration of the protein in the filtrate equals the concentration of the protein in the feed and the retentate, a sieving coefficient of 100% is obtained. Furthermore, the sieving coefficient allows to determine the nominal cut-off of a membrane (corresponding to 10% of sieving coefficient).

$$S = \frac{2C_F}{C_{Bin} + C_{Bout}}$$

where $C_F$ is the concentration of a solute in the filtrate;

$C_{Bin}$ is the concentration of a solute at the blood inlet side of the device under test;

$C_{Bout}$ is the concentration of a solute at the blood outlet side of the device under test.

For the purposes of the present invention, the preferred membrane allows for passage of molecules in the range of toxic mediators of up to 45,000 Daltons in the presence of whole blood/blood proteins, which means the molecular weight of a substance having a sieving coefficient (S) of 0.1 to 1.0 in presence of whole blood.

As used herein the term "cut-off" refers to molecular weight of a substance having a sieving coefficient (S) of 0.1.

As used herein, the term "hemodialysis", HD, refers to a process to correct the chemical composition of blood by removing accumulated metabolic products and adding buffer in a process of diffusion through a natural or synthetic semipermeable membrane.

As used herein, the term "hemodiafiltration", HDF, refers to a process to remove accumulated metabolic products from blood by a combination of diffusive and convective transport through a semi-permeable membrane of high-flux type; fluid is removed by ultrafiltration and the volume of filtered fluid exceeding the desired weight loss is replaced by sterile, pyrogen-free infusion solution.

As used herein, the term "hemofiltration", HF, refers to a process of filtering blood by a membrane with separation of plasma water and solutes with the ultrafiltrate, and retains all proteins larger than effective pore size and blood cells. In hemofiltration the accumulated metabolic products are removed from the blood by the process of convective transport as a consequence of ultrafiltration through a semi-permeable membrane of high-flux type; the volume of filtered fluid exceeding the desired weight loss is replaced by sterile pyrogen-free infusion solution.

As used herein, the term "ultrafiltrate" refers to the filtered plasma water and solute and molecules (including free light chains) smaller than effective pore size.

Methods of producing suitable membranes are disclosed in, for example, WO 2004/056460. Such membranes are discussed herein as Gambro membranes, for example by their reference "Gambro dialyser HCO 1100".

Super flux membranes, such as Toray BK 21-F and BG 2.10, may also be used, but these do not work as efficiently as the Gambro HCO membrane.

Preferably, the subject has a malignant B cell disease, such as multiple myeloma or AL amyloidosis.

The method of the invention is preferably carried out in combination with treatment of the malignant B cell disease. The treatment of the malignant B cell disease decreases the production of free light chains by the subject. The method of the invention removes at least a portion of the free light chain in the blood, resulting in decreased kidney damage and increases the chance of renal recovery in the subject.

Methods of treating malignant B cell diseases are themselves known in the art, such as the use of one or more of dexamethasone, bortezomib and/or adriamycin (doxorubicin). For example, cyclophosphamide, thalidomide and dexamethasone may be used, or vincristine, adriamycin and dexamethasone.

The light chain dialysis may be λ and/or κ. κ light chains are more efficiently dialysed. λ forms dimers in blood and is therefore larger.

The surface area of the membrane exposed to the blood from the subject may be increased either by using two or more dialysers in series or to increase the membrane surface area in one dialyser cartridge. The most effective surface depends on the blood flow which is applied. For blood flows in a range of 250 and 300 ml/minute the best suitable surface area is in the range of up to 2 m². (see FIG. 7) This has been found to increase the rate of free light chains removed from the blood by the dialysis membrane. Dialysis membranes are conventionally provided in cartridges having an inlet and outlet for blood, and inlet and outlet for dialysis fluid and spent dialysate. Hence, two or more cartridges may be used, the blood passing through a first cartridge and then to a second cartridge.

The method may comprise an additional step of subjecting either the subject's blood, or a dialysate fluid used during the haemodialysis step, to an assay capable of detecting free light chains. In the case where the assay suggests that a dialysis membrane used in the haemodialysis step is at least partially blocked, the dialysis membrane may be replaced or the haemodialysis step terminated. The free light chains may be measured and an observed reduction in the rate of removal of free light chains gives an indication that a membrane may be becoming blocked. The assay may also be used to estimate the amount of free light chain removed during dialysis and indicate the effect of the dialysis treatment on the disease causing the excess free light chain. It may also be used to assist in monitoring the effect of drugs on free light chain production in the patient.

Methods of detecting free light chains are known in the art, as shown, for example, in the article by Bradwell, et al. (2002) and the book by the same author (Supra).

A further aspect of the invention provides an assay for determining the effect of the method of reducing free light chain in a subject by the method of the invention, comprising providing a sample of blood, serum, dialysate or ultrafiltrate from the subject, and determining an amount of free light chains in the sample.

Preferably the assay compares the amount of free light chain in the sample with an amount identified in a sample taken earlier in the treatment of the subject. A decrease in the amount between the earlier sample and the later sample is indicative that the method of the invention is removing free light chains from the blood of the subject.

According to a further aspect of the invention, there is provided the use of a dialysis membrane, in the preparation of a haemodialysis unit for conducting haemodialysis on a subject to reduce blood free light chain concentration in the patient. Advantageously, the use of such a membrane in the preparation of the haemodialysis unit allows dialysis to be used for the effective removal of free light chains from the blood serum of the subject, with the result that the pre-renal FLC load is reduced and, therefore, that renal failure is prevented or slowed.

The subject may be a mammal and is preferably a human subject.

The dialysis membrane may be as defined above for the first aspect of the invention and may have a molecular weight cut-off greater than about 45 kDa in blood or blood plasma. Preferably, the dialysis membrane is of a type discussed in WO 2004/056460 and as defined above.

The term "comprising" is intended to mean that, for example, the methods or assays of the invention may have additional, e.g. optional, steps. The methods and assays are not limited to methods and assays restricted to just the steps specifically indicated.

EXAMPLES

Embodiments of the invention will now be shown, by way of example only, with reference to Tables, 1-5, and FIGS. 2-8. Serum and dialysate concentrations of free light chains in the examples below were determined by standard free light chain assays available under the trademark "Freelite" from The Binding Site Ltd., Birmingham, UK. However, other methods of detecting the concentration of free light chains, which are known in the art, could also have been used.

Patients and Methods

This study was approved by the Solihull and South Birmingham Research Ethics Committees and the Research and Development Department of the University Hospitals Birmingham NHS Foundation Trust. All patients gave informed and written consent.

Study Design and Participants

The study comprised:—1) An initial in-vitro and in-vivo assessment of dialysers for clearance of FLCs, 2) Development of a compartmental model for FLC removal based upon observed dialysis results and 3) Use of the model and the most efficient dialyser to determine the optimal strategy for removal of FLCs from patients with renal failure complicating multiple myeloma. The patients investigated were those attending or referred to the nephrology department at the Queen Elizabeth Hospital, Birmingham, UK.

In-Vitro Assessment of FLCs Removal by Isolated Ultrafiltration

Seven dialysers were assessed for filtration efficiency (Table 1). Each was placed in a simple circuit and primed with one litre of normal saline. One litre of serum containing 1,000 mg of both monoclonal κ and λ FLCs was then re-circulated through the dialysers at 400 ml/min, with a trans-membrane pressure of 300-400 mmHg. The procedure was stopped when production of ultra-filtrate (UF) fluid ceased. The dialysers were finally flushed with one litre of fresh saline to remove fluid containing any residual protein. The quantities of FLCs in the filtered serum, UF and flushed fluid were calculated from the FLCs concentrations and measured volumes. Serum FLC reductions were calculated by subtracting the final FLC concentrations from the initial values. The percentage of the original 1,000 mg of each FLC, present in the UF at the end of the experiment, was calculated to determine the ability of the membrane to filter FLCs. These assessments were repeated three times for each dialyser and the mean values determined.

In-Vitro Assessment of FLC Removal by Hemodialysis

The two dialysers that filtered most FLCs, the Toray BK-F 2.1 and the Gambro HCO (high cut-off) 1100, were assessed, in-vitro, for dialysis efficiency. Gambro HCO membranes are of the type disclosed in WO 2004/056460. Each dialyser was connected to a Gambro AK 90 hemodialysis machine and primed with one litre of normal saline. One litre of serum containing 1,000 mg of both κ and λ FLCs was then dialysed for four hours. Serum flow rates were set at 300 mls/min, dialysate flow rates at 500 mls/min, and trans-membrane pressures at 0-10 mm/Hg while the serum volumes were maintained at one litre with no ultrafiltration. After two hours, the serum was spiked with 24 ml of saline containing a further 1,000 mg of both κ and λ FLCs in order to assess dialyser blockage. Serum and dialysate fluids were sampled at short intervals for the FLC measurements. Clearance values for κ and λ were calculated as follows:

$$\text{Clearance (ml/min)} = \frac{\text{dialysate concentration of } FLCs}{\text{Inlet serum concentration of } FLCs} \times \text{dialsyate flow rate}$$

Mean dialysate concentrations of FLCs and clearance rates were calculated from both pre-and post-spike samples, for both dialysers and significant differences assessed.

In-Vivo Assessment of FLC Removal in Patients with Multiple Myeloma

During the study period, 13 patients with dialysis-dependent renal failure (eGFR<15 mls/min/1.73 m$^2$) and multiple myeloma presented to the Nephrology Department. The first three patients were dialysed on one or more of the following dialysers: B. Braun Hi-PeS 18; Toray BK-F 2.1 and Gambro HCO 1100 to determine their individual efficiency for FLC clearance. Subsequent patients were dialysed only on the Gambro HCO 1100 because of its superior FLC clearance rates (Tables 3 and 4). Patients 4 and 5 had routine dialysis, 4 hours, thrice weekly. Extended hemodialysis with the Gambro HCO dialyser was evaluated in patients 6-8. Daily extended hemodialysis on the Gambro HCO dialyser was evaluated for FLC removal in patients 9-13 who presented with acute cast nephropathy.

Serum and dialysate concentrations of FLCs were measured at short intervals during the dialysis sessions. Percentage serum reductions in FLCs, mean dialysate concentrations (mg/L), dialysate FLC content per hour of dialysis (g/hr) and clearance rates (ml/min) were calculated. For the first three patients these results were compared for each membrane.

Evaluation of FLC Removal by Extended Hemodialysis on the Gambro HCO 1100

An extended dialysis regimen of up to 12 hours was evaluated in eight patients (6-13) with dialysate flow rates of between 300-500 ml/min and blood flow rates of 150-250 ml/min were used. Some patients were treated with two or three dialysers in series (Table 4). The following correlations were assessed: Serum FLC concentrations with quantity of FLC in the dialysate; serum reductions with duration of dialysis; clearance rates with dialysate flow rates and dialyser surface area. Cardiovascular stability was monitored throughout each dialysis session. Serum FLCs, albumin and electrolyte concentrations were measured pre-and post-dialysis.

Therapeutic Extended Daily Hemodialysis on the Gambro HCO 1100 for Patients with Cast Nephropathy During the study period, five patients (9-13) presented with new multiple myeloma, acute renal failure and biopsy proven cast nephropathy. An extended, daily, dialysis regimen was undertaken in an attempt to rapidly reduce sFLC concentrations. All patients received induction chemotherapy using local haematology protocols. FLC clearance rates were evaluated with dialysate flow rates of between 300-500 ml/min and blood flow rates of 150-250 ml/min. Patients were assessed daily to determine fluid balance with the aim of maintaining euvolaemia. Ultrafiltration was used in addition to hemodialysis when there was fluid overload and intravenous infusions were used to correct dehydration. Cardiovascular stability was monitored throughout each dialysis session. Serum FLCs, albumin and electrolyte concentrations were measured pre-and post-dialysis. Serum immunoglobins were measured to assess immune status and normal human immunoglobins (NHIG) were given, at 0.5 g/kg body weight, when serum IgG concentrations were less than 5 g/L.

Laboratory Measurements of FLCs

Serum and dialysate, κ and λ FLC concentrations were measured by nephelometry, on a Dade-Behring BNII™ Analyser, using a particle-enhanced, high specificity homogeneous immunoassay (FREELITE™, The Binding Site, Birmingham, UK). Normal serum ranges used were κ: 7.3 mg/L (range 3.3-19.4) and λ: 12.7 mg/L (range 5.7-26.3) (20).

Mathematical Model of FLC Removal in Patients with Multiple Myeloma

Figure 2:
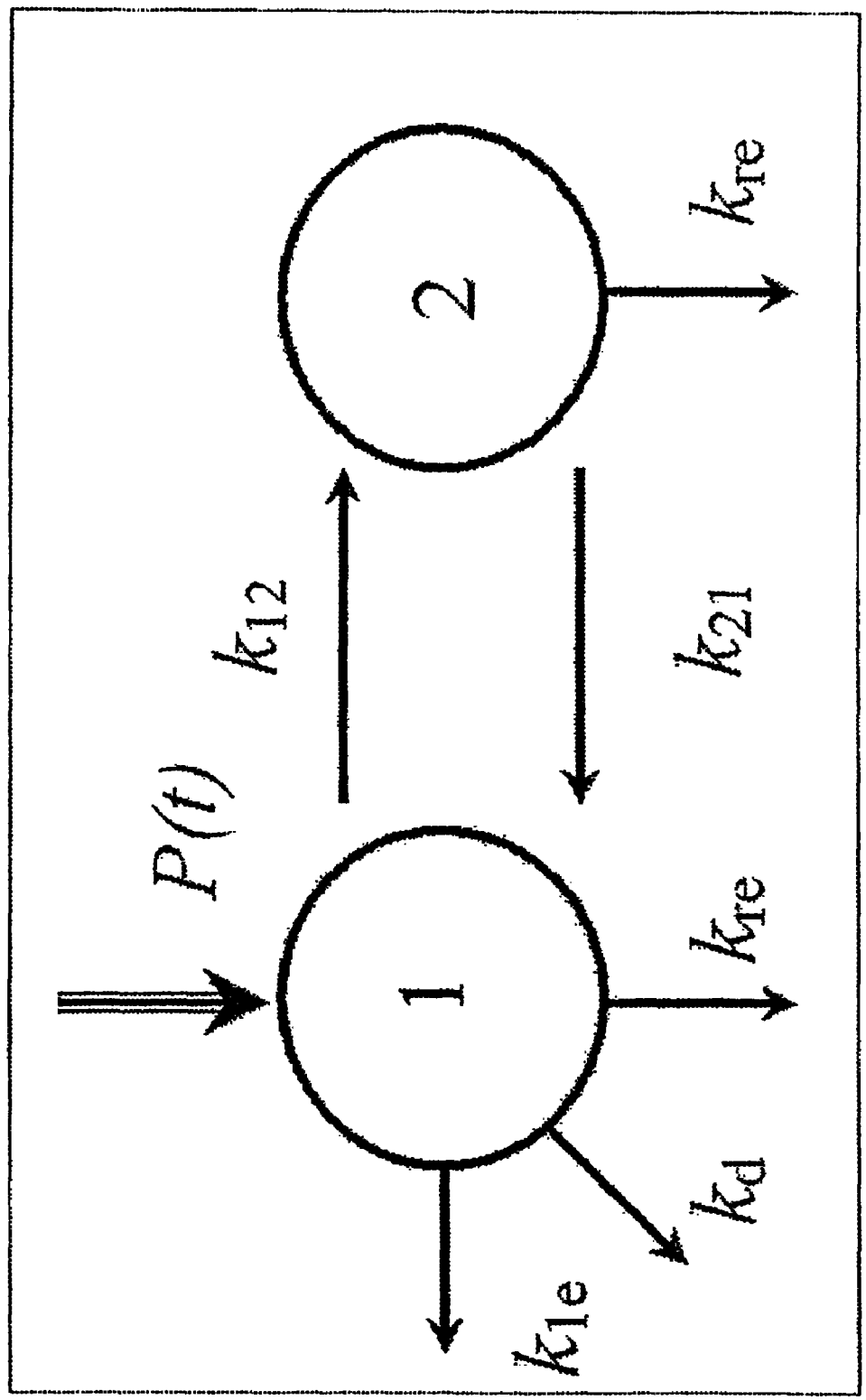
FIG. 2 shows free light chain (FLC) compartmental model. Parameters were as follows: P(t)—FLC production rate (23.15 mg/min). $k_{1e}$—Elimination rate due to renal function (0 mg/min). $k_d$—Elimination rate due to dialysis ($1.5 \times 10^{-2}$/min$^{-1}$). $k_{12}$—Rate constant of FLC flow between plasma and extravascular compartment ($2.15 \times 10^{-2}$/min). $k_{21}$—Rate constant of FLC flow between extravascular compartment and plasma ($4.3 \times 10^{-3}$/min). $k_{re}$—Elimination rate due to the reticuloendothelial metabolism ($1.6 \times 10^{4}$/min). Plasma compartment volume 2.5 L. Extravascular compartment volume 12 L.

A two-compartment mathematical model of FLC production, distribution and removal in multiple myeloma was constructed to compare the efficiencies of plasma exchange and hemodialysis (FIG. 2). This was similar in structure to models for dialysis removal of urea and beta-2-microglobulin (Depner T. A., Prescribing dialysis: Guide to urea modelling, Klower Academic Publishers (1990) and Ward R. A., et al., Kid. Int. (2006), 1431-1437). It consisted of intra-vascular and extra-vascular compartments (1 and 2 respectively) with flow of FLCs into, between and out of each compartment. The renal clearance of sFLC was considered zero (eGFR=0) in patients with renal failure. Under such conditions, removal was by the reticuloendothelial system only, with a half-life of 3 days. Using this half-life, a production rate of 33.8 g/day produced a steady state of 10 g/L in the intra-vascular compartment. This was a suitable starting value for the clearance simulations.

Data from a multiple myeloma patient was analyzed using the model within the software package FACSIMILE (Curtis A. R., Harwell Laboratory Report AERE 12805 (1987) in order to generate rates of serum FLC removal. Simulations were then conducted to compare plasma exchange treatments (over 10 days) with 5 hemodialysis protocols for hypothetical patients. For convenience we set the initial serum FLC concentrations at 10,000 mg/L with chemotherapeutic tumor killing of 0%, 2%, 5% and 10% per day, and 100% on the first day (Table 5).

Statistical Analysis

Results of the different dialysers for in vitro and vivo studies of FLC removal by hemodialysis were compared using Student's T-test (2 tails, type 2) for significant differences. $P<0.05$ was consider statistically significant.

Results

In-Vitro Assessment of Isolated Ultrafiltration

The efficiencies of the different dialysers for removal of FLCs are shown in Table 1. All dialysers caused substantial reductions of FLC concentrations in the circulated serum. Varying amounts of FLCs were identified in UF and it is assumed that the amounts missing were bound to the membranes. The Gambro HCO 1100 was the most efficient dialyser with only small amounts of FLCs bound to the membranes.

TABLE 1

Efficiency of dialysers for in-vitro removal of FLCs by isolated ultrafiltration.

| Class | Make | Model | Membrane material | Surface Area (m²) | Cut off in blood (kDa)* | Mean reduction in FLCs (%) | | Mean FLCs concentration in UF(%) | |
|---|---|---|---|---|---|---|---|---|---|
| | | | | | | κ | λ | κ | λ |
| High-flux | B. Braun | Hi-PeS 18 | PES | 1.8 | 10 | 54 | 39 | 17 | 12 |
| | Asahi | APS-1050 | PS | 2.1 | 10⁺ | 71 | 65 | 30 | 18 |
| | Nikkiso | FLX 8GWS | PEPA | 1.8 | 10⁺ | 68 | 45 | 12 | 11 |
| | Idemsa | 200 MHP | PES | 2.0 | 10⁺ | 67 | 59 | 21 | 16 |
| Super-flux | Toray | BK-F 2.1 | PMMA | 2.1 | 20 | 88 | 73 | 0.1 | 0.2 |
| | Toray | BG 2.1 | PMMA | 2.1 | 20 | 71 | 41 | 0.1 | 0.1 |
| High cut-off | Gambro | HCO 1100 | PAES | 1.1 | 45 | 96 | 94 | 62.5 | 90 |

UF: ultrafiltrate.
*Pore sizes obtained from the manufacturer's data sheets.
⁺This is an approximate size; manufacturer's data not available.
PES (polyethersulfone);
PS (Polysulfone);
PEPA (polyester polymer alloy);
PMMA (polymethyl methacrylate);
PAES (polyarylethersulfone).

In-Vitro Assessment of Hemodialysis

The results for FLC removal by in-vitro hemodialysis using the Toray BK-F 2.1 and the Gambro HCO 1100 dialysers are shown in Table 2. Significantly higher FLC dialysate concentrations and greater serum reductions were achieved using the Gambro HCO dialyser. Clearance rates of both FLCs were 60-fold higher using the Gambro dialyser compared with the Toray dialyser.

TABLE 2

Efficiency of dialysers for in-vitro removal of FLCs by hemodialysis during four hours.

| Membrane | Test samples | Pre-spike % removed κ | Pre-spike % removed λ | Post-spike % removed κ | Post-spike % removed λ | Mean % removed κ | Mean % removed λ | Clearance rates (ml/min) κ | Clearance rates (ml/min) λ |
|---|---|---|---|---|---|---|---|---|---|
| Toray BK-F 2.1 | Serum | 77.9 | 75 | 88.8 | 84.3 | 81.5 | 78 | 0.59 (0.02-1.6) | 0.47 (0.02-1.4) |
| | Dialysate fluid | 0.63 | 0.87 | 2 | 2.2 | 1.3 | 1.54 | | |
| Gambro HCO 1100 | Serum | 95 | 93 | 96 | 95 | 95.5* | 94* | 35.1* (7.5-50.9) | 32.2* (19.1-45.9) |
| | Dialysate fluid | 50 | 88 | 75 | 93 | 62.5* | 90* | | |

*Gambro dialyser significantly more efficient ($p < 0.02$).

In-Vivo Use of Dialysers for FLC Removal in Patients with Multiple Myeloma

The clinical details of patients studied for FLC removal are summarised in Table 3. All were in dialysis-dependent renal failure. FLC removal by hemodialysis was evaluated for three different dialysers in the first three patients. Details of the dialysis periods and the amounts of FLCs removed are shown in Table 4. For example, in patient 2, the Gambro HCO 1100 resulted in greater reductions in serum FLC concentrations (58.5%) than either the B. Braun Hi-Pes 18 (5.6%, $p<0.002$) or the Toray BK-F 2.1 (24.2%, $p<0.001$). The average dialysate concentrations of FLCs, were many times higher during the dialysis sessions using the Gambro HCO 1100, i.e., 266 mg/L, compared with 5 mg/L using the B. Braun Hi-Pes 18 ($p<0.02$) and 2 mg/L using the Toray BK-F 2.1 ($p<0.004$). Later patients (4-13) were only treated with the Gambro HCO 1100 dialyser.

TABLE 3

Clinical details of multiple myeloma (MM) patients treated by hemodialysis.

| Patient | Age | Myeloma type | Presentation FLC concentrations (mg/L) | Chemotherapy regime | Renal diagnosis | Adverse events | Supportive therapy | Clinical outcomes |
|---|---|---|---|---|---|---|---|---|
| Evaluation of FLC removal by hemodialysis ||||||||||
| 1 | 61 | New IgGλ | 17,000 | CThal Dex | ARF, no biopsy | *C. diff* | Nil | Renal recovery |
| 2 | 73 | Relapsing IgGλ | 1,780 | CThal Dex | CKD, no biopsy | Bone fractures | Nil | ESRF |
| 3 | 42 | New FLC κ | 6,980 | CThal Dex | ARF, cast nephropathy | AL amyloidosis | Albumin | ESRF |
| 4 | 77 | New IgGλ | 5,140 | Cyc and Dex | ARF, no biopsy | Septicemia | Albumin | Died of MRSA septicemia |
| 5 | 59 | New IgGκ | 734 | Thal Dex | CKD, no biopsy | Nil | Albumin | Dialysis dependent |
| 6 | 78 | New FLC λ | 15,900 | CThal Dex | CKD, severe interstitial fibrosis | Nil | Albumin | ESRF |
| 7 | 70 | Relapsing FLC λ | 7,950 | Idarubicin, Dex, Cyc | ARF, no biopsy | *C. diff*, and septicemia | Albumin, NHIG | Died from neutropenic sepsis |
| 8 | 63 | New IgGλ | 656 | Dex | ARF, ATN | Nil | Nil | Renal recovery |
| Extended Daily Haemodialysis for Cast Nephropathy ||||||||||
| 9 | 68 | MGUS → IgGκ | 1,030 | CThal Dex | ARF, cast nephropathy | Nil | Albumin | Renal recovery eGFR at 6 months 49 |
| 10 | 51 | New IgAκ | 42,000 | VAD | ARF, cast nephropathy | Nil | Albumin, NHIG prophylactic antibiotics, GCSF | Dialysis dependent |
| 11 | 61 | New IgAκ | 13500 | Thal Dex | ARF, cast nephropathy | Nil | Albumin, NHIG | Renal recovery eGFR at 6 weeks 29 |

TABLE 3-continued

Clinical details of multiple myeloma (MM) patients treated by hemodialysis.

| Patient | Age | Myeloma type | Presentation FLC concentrations (mg/L) | Chemotherapy regime | Renal diagnosis | Adverse events | Supportive therapy | Clinical outcomes |
|---|---|---|---|---|---|---|---|---|
| 12 | 68 | New IgGλ | 1120 | Thal, Dex | ARF, cast nephropathy | *C. diff.*, lobar pneumonia and ACS | Albumin, NHIG | Ongoing treatment |
| 13 | 81 | New IgGλ | 2110 | Dex, Cyc | ARF, cast nephropathy | Nil | Albumin, NHIG | Renal recovery eGER at 2 weeks 28 |

ACS (acute coronary syndrome);
ARF (acute renal failure);
ATN (acute tubular necrosis;
*C. diff* (*Clostridium difficile*);
CKD (chronic kidney disease);
CThalDex (cyclophosphamide, thalidomide and dexamethasone);
Thal Dex (thalidomide and dexamethasone);
Cyc (cyclophosphamide);
Dex (dexamethasone);
ESRF (end stage renal failure;
an eGFR <10 mls/min/1.73 $m^2$);
eGFR (estimated glomerular filtration rate by Cockfroft-Gault equation in mls/min/1.73 $m^2$);
GCSF (granulocyte colony stimulating factor);
MGUS (monoclonal gammopathy of undetermined significance evolved to MM);
MRSA (methicillin resistant *Straphylococcus aureus*);
NHIG (normal human immunoglobulins);
VAD (vincristine, Adriamycin (doxorubicin), dexamethasone).

TABLE 4

Summary of free light chain (FLC) removal by hemodialysis in patients with multiple myeloma.

| Patient | FLC | Dialyser make (number) | | No of dialysis sessions | Mean (range) length of dialysis sessions in hours | Mean pre-dialysis serum concentration (mg/L) | Mean % reduction in serum concentrations | Mean (range) dialysate concentration (mg/L) | Mean dialysate content per hour of dialysis (g/hr) | Mean clearances (ml/min) | % FLC reduction achieved |
|---|---|---|---|---|---|---|---|---|---|---|---|
| \multicolumn{12}{c}{Evaluation of FLC removal by hemodialysis} |
| 1 | λ | Toray BK-F2.1 | | 7 | 3.6 (2-4) | 11,580 | 3.2 | 6.9 (0.8-20.3) | 0.2 | 0.29 | N/A |
| 2 | λ | B. Braun Hi-Pes 18 | | 2 | 3.75 (3.5-4) | 1,795 | 5.6* | 5.3* (2.7-9.5) | 0.16* | 1.5* | |
| | | Toray BK-F 2.1 | | 3 | 4 | 2,950 | 24.2* | 2* (0.5-3.5) | 0.06* | 0.5* | |
| | | Gambro HCO 1100 | | 2 | 4 | 9,155 | 58.5 | 265.6 (88-648) | 7.8 | 22 | |
| 3 | κ | Toray BK-F 2.1 | | 4 | 3.6 (3-4) | 8,002 | 22.5* | 11.1* (6.4-30.4) | 0.72* | 1.6* | |
| | | Gambro HCO 1100 | | 6 | 4 | 2,880 | 44.5 | 163 (120-219) | 4.9 | 30.4 | |
| 4 | λ | Gambro HCO 1100 | | 6 | 2.9 (2-4) | 3,361 | 23.6 | 101 (36-241) | 3.2 | 15.6 | |
| 5 | κ | Gambro HCO 1100 | | 3 | 3.3 (2-4) | 536 | 57.9 | 7.1 (4.2-9.9) | 0.2 | 14.8 | |
| 6 | λ | Gambro HCO 1100 | | 10 | 4.6 (4-6) | 10,548 | 58.9 | 219 (65-843) | 6.6 | 16.2 | |
| 7 | λ | Gambro HCO 1100 | | 11 | 6.9 (2-11) | 4,651 | 57.8 | 137 (28.6-411) | 2.6 | 16.8 | |
| 8 | λ | Gambro HCO 1100 | | 3 | 10.7 (10-12) | 494 | 53.8 | 18 (8-37.3) | 0.3 | 15.9 | |
| \multicolumn{12}{c}{Extended Daily Haemodialysis for Cast Nephropathy} |
| 9 | κ | Gambro HCO 1100 | | 13 | 4.8 (2-8) | 445 | 45 | 18.1 (1.6-56) | 0.37 | 17.1 | 90 |
| 10 | κ | Gambro HCO | (1) | 12 | 7.25 (1-10) | 22,408 | 36 | 439 (15-1610) | 9.7 | 9.2 | 50 |
| | | 1100 | (2) | 6 | 6.5 (6-8) | 17,610 | 57 | 514 (187-1370) | 15.7 | 25.6 | |
| | | | (3) | 1 | 8 | 18,800 | 75 | 515 (151-1810) | 11.6 | 31.5 | |
| 11 | κ | Gambro HCO | (1) | 2 | 9 (6-12) | 12,850 | 35.1 | 307 (200-414) | 5.6 | 11.6 | 90 |
| | | 1100 | (2) | 20 | 6.3 (3-10) | 6,887 | 81 | 193 (53-409) | 5.7 | 25.5 | |
| 12 | λ | Gambro HCO | (1) | 2 | 9 (6-12) | 1,004 | 66.4 | 34 (21-47) | 0.6 | 28.5 | 0 |
| | | 1100 | (2) | 46 | 6.3 (4-10) | 1,157 | 80.4 | 46 (21-91) | 1.3 | 42.9 | |
| 13 | λ | Gambro HCO | (1) | 2 | 5 (4-6) | 1,357 | 58 | 28.9 (9-48) | 0.8 | 13.5 | 90 |
| | | 1100 | (2) | 12 | 6.3 (6-10) | 397 | 74 | 13.7 (6-26) | 0.25 | 33 | |

*Significantly less than the Gambro HCO 1100 result for this patient (p < 0.02).

Evaluation of FLC Removal by Extended Hemodialysis on the Gambro HCO 1100

Extended hemodialysis (>4 hours) on the Gambro HCO 1100 was evaluated in patients 6-13 for FLC removal (Table 4). The procedure was well tolerated with no cardiovascular complications. During sessions, there was a mean serum albumin reduction of 3.9 g/L (p<0.03) that was replaced routinely with 20% albumin solution. Calcium and magnesium were replaced as required. Measurements indicated that there was no IgG leakage into the dialysate fluid.

Figure 3:
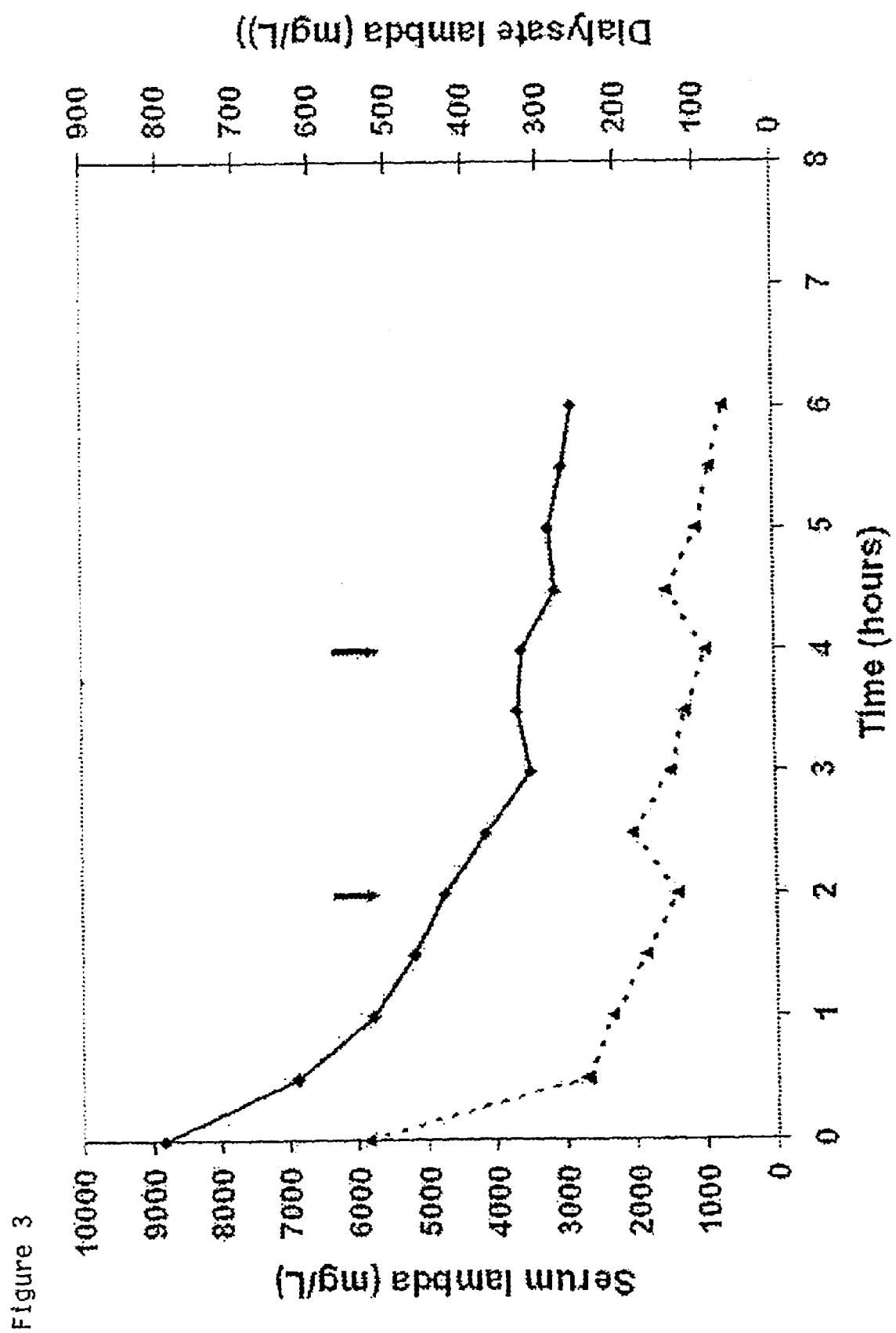
FIG. 3 shows serum (diamonds) and dialysate (triangles) lambda FLC concentrations over a 6 hour hemodialysis session using Gambro HCO 1100 dialysers (Patient 6). Arrows indicate use of a new dialyser.
Figure 4:
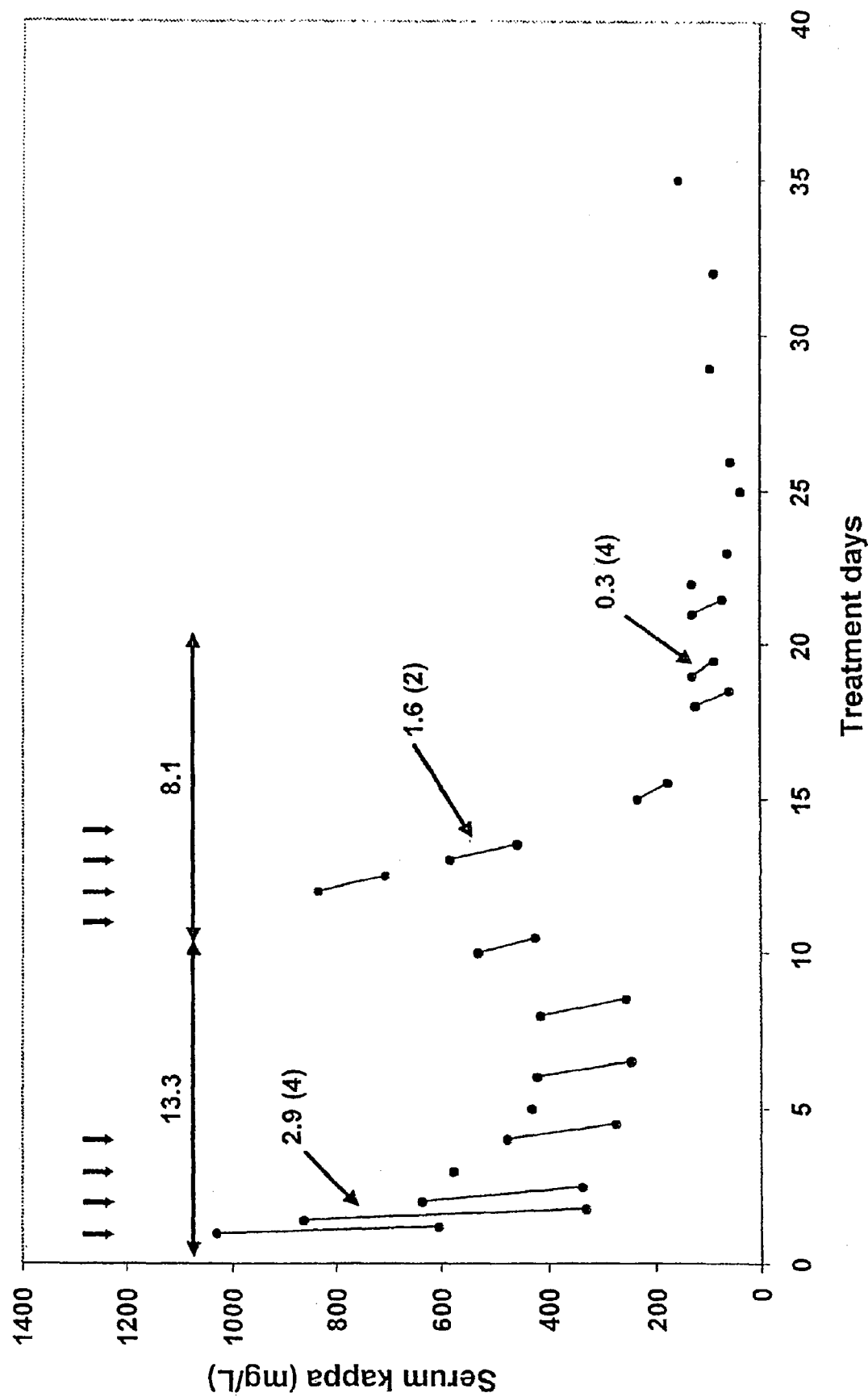
FIG. 4. Patient 9 shows pre-and post-dialysis kappa FLC concentrations. Numbers on the figure are the amounts of κ removed in the dialysate per 10 day period in grams. Arrows highlight the removal during individual sessions (in brackets is the duration of dialysis session in hours). The arrows correspond to daily doses of dexamethasone. In addition, the patient received daily thalidomide. The patient's last dialysis session was on day 26 and he has been dialysis independent for 6 months.
Figure 5:
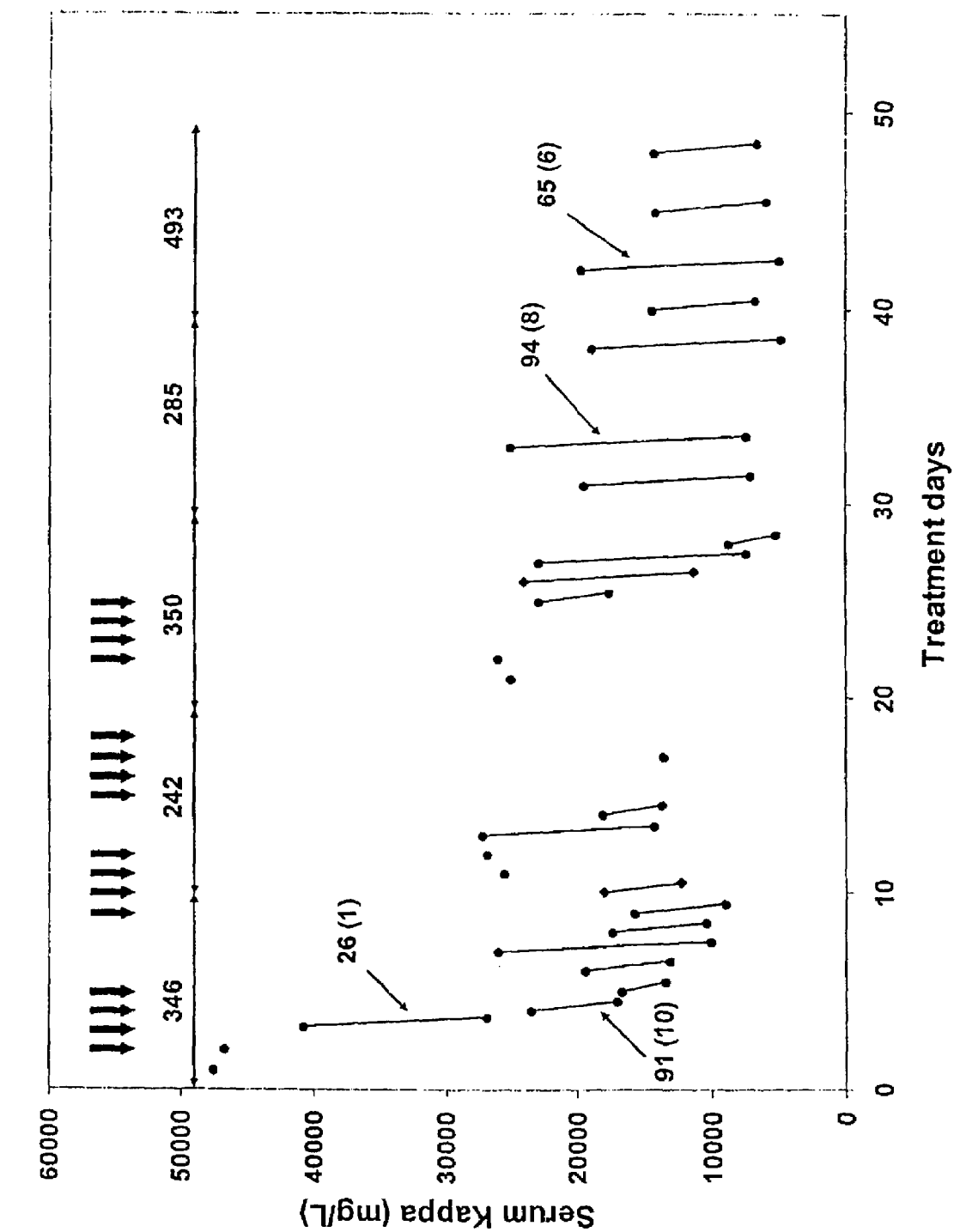
FIG. 5. Patient 10 shows pre-and post-dialysis kappa FLC concentrations. Numbers on the figure are the amounts of κ removed in the dialysate per 10 day period in grams. Arrows highlight the removal during individual sessions (in brackets is the duration of dialysis session in hours). The arrows correspond to daily doses of dexamethasone. The patient had a failed trial without dialysis between days 18 and 27.
Figure 6:
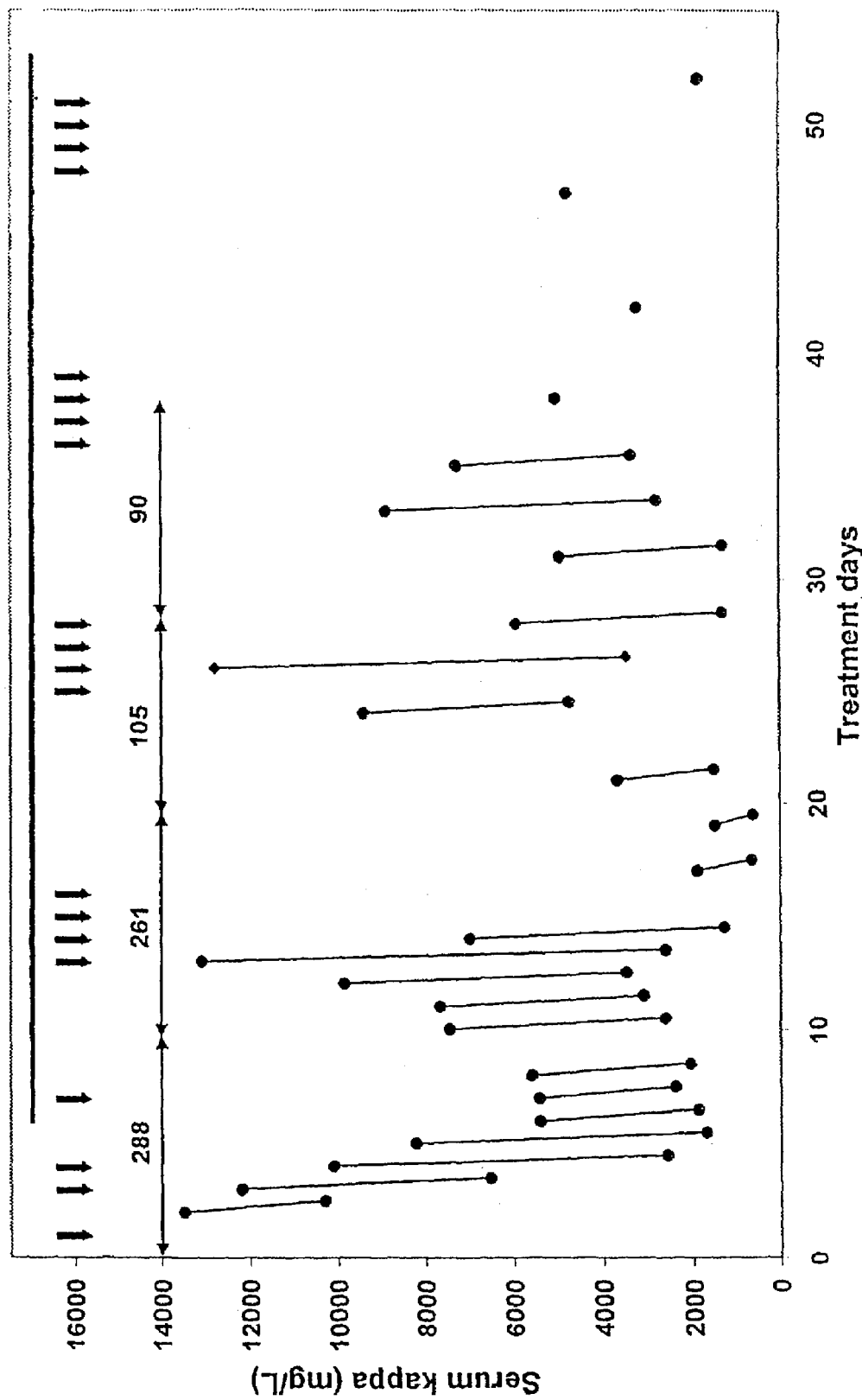
FIG. 6. Patient 11 shows pre-and post-dialysis kappa FLC concentrations. The arrows correspond to daily doses of dexamethasone. In addition, the patient received daily thalidomide (solid line). The patient's last dialysis session was on day 35 and he has been dialysis independent for 6 weeks.

In all patients, pre-dialysis serum FLC concentrations correlated with the amounts removed in the dialysate fluids (R=0.74: p<0.0001). FIG. 3 shows serum and dialysate FLC concentrations during a 6-hour session for patient 6. When the dialyser was replaced, there was a transient increase in FLC removal. FIGS. 4, 5 and 6 show the daily pre-and post-dialysis serum FLC concentrations and the amounts in the dialysate fluids for patients 9, 10 and 11, together with details of chemotherapy.

There was a significant correlation between percentage serum FLC reduction and the time on hemodialysis for all patients (R=0.53: p<0.001). Mean clearance rates of FLCs varied from patient to patient: κ ranged from 9.2-31.5 mls/min and λ 13.5-42.9 mls/min. In eight patients, where data was available, clearance rates of serum FLCs correlated with dialysate flow rates (R=0.58: p<0.0001). At flow rates of 300 ml/min, the clearance was 10.8 ml/min (range 5.2-22.6) compared with 19.3 ml/min (range 7.2-39.8) at 500 ml/min. Dialyser surface area was also related to FLC clearance rates. For example, patient 10 was dialysed on separate occasions on one, two or three dialysers, in series, with progressive increases in FLC clearance rates (Table 4 and FIG. 7). The albumin loss in the dialysate increased significantly with each additional dialyser (one: 0.16 g/L, two: 0.44 g/L, three: 0.58 g/L). Measurement of dialysate κ FLC concentrations over a six-week period indicated removal of 1.7 kg. Daily measurements of removal by hemodialysis and urine excretion plus estimated internal metabolism indicated a production rate of 150-200 g/day.

Therapeutic Extended Daily Hemodialysis on the Gambro HCO 1100 for Patients with Cast Nephropathy During the study period five unselected patients presented with new multiple myeloma and cast nephropathy (patients 9-13). All patients were dialysis dependent and were given dexamethasone based induction chemotherapy. They were treated with an intensive extended dialysis schedule of between 13 and 48 dialysis sessions, ranging from 2-12 hours. Initially patients were dialysed on one dialyser for one or two sessions and then two dialysers in series. In the first week we attempted to dialyse the patients on a daily basis and subsequently on alternate days. In all patients, extended haemodialysis resulted in consistent significant reductions in serum FLC concentrations and large quantities were present in the dialysate fluids (Table 4).

Three of the five patients treated with extended daily hemodialysis became independent of dialysis. The chemotherapy of patients 10 and 12 was withheld because of recurrent infections. Although, dialysis removed significant quantities of FLC they continued to have large rebounds in serum concentrations post-dialysis and they remained dependent on dialysis. By comparison, the three patients who became dialysis independent (9, 11 and 13) responded rapidly to the induction chemotherapy with less ongoing production of FLCs (e.g. FIGS. 4 and 6).

Simulation Model For FLC Removal

Figure 8:
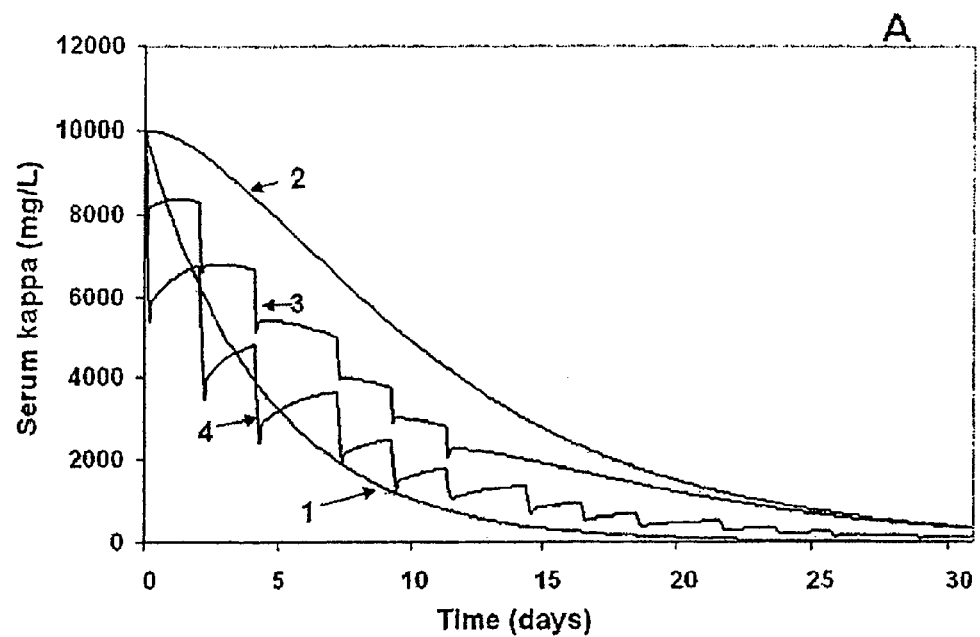
FIG. 8A & B. Simulations of serum free light chain (FLC) removal by plasma exchange versus hemodialysis on the Gambro HCO 1100. Simulations: 1) 100% tumour kill on day one with only reticulo-endothelial system removal. 2) 10% tumour kill per day with reticulo-endothelial system removal alone. 3) 10% tumour kill per day with plasma exchange (3.5 litres exchange in 1.5 hrs.×6 over 10 days). 4) 10% tumour kill per day with hemodialysis for 4 hours, three times a week. 5) 10% tumour kill per day with hemodialysis for 4 hours per day. 6) 10% tumour kill per day with hemodialysis for 12 hours per day. 7) No tumour kill with 8 hours hemodialysis on alternate days. 8) No tumour kill with no therapeutic FLC removal.
Figure 8:
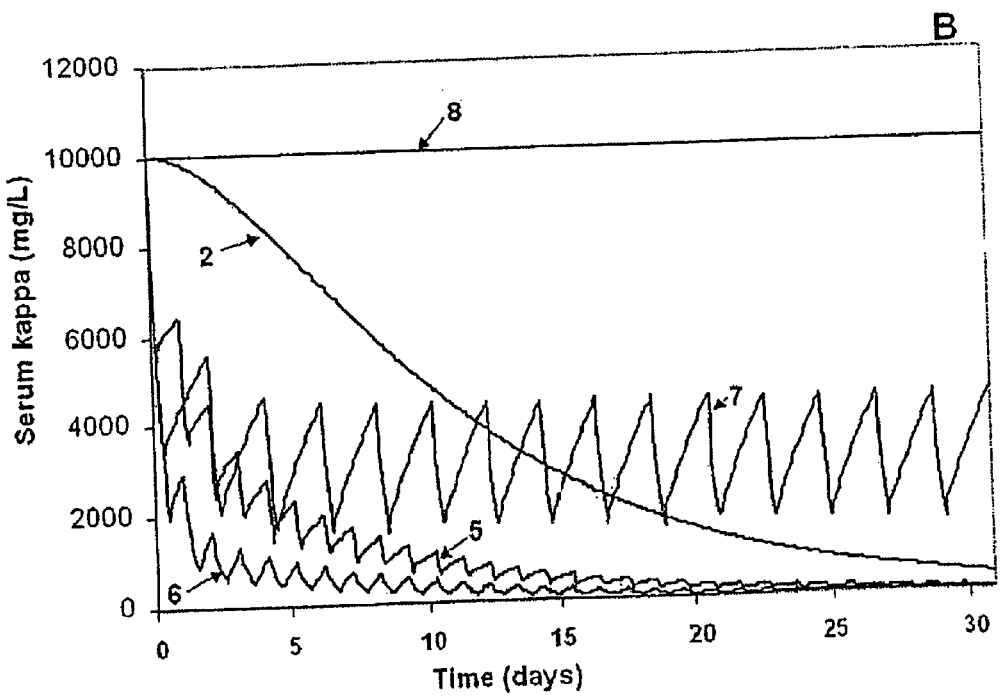

The results of the simulation studies are shown in Table 5 and FIG. 8. With complete tumor killing on day one (simulation 1), serum FLCs were >500 mg for two weeks (assuming no therapeutic FLC removal). With a chemotherapeutic tumor kill rate of 10% per day and no dialysis, serum FLC concentrations remained elevated on day 30 (simulation 2). Plasma exchange (simulation 3) was less effective in reducing serum FLCs than hemodialysis for 4 hours, ×3 per week using the Gambro HCO 1100 dialyser (simulation 4) and neither method was rapid. Extended daily dialysis (for 12 hours) reduced FLC concentrations to 5% of the starting concentrations in five days (simulation 6) compared with 29 days for plasma exchange (simulation 3). Analysis of the FLC load on the kidneys over 3 weeks (area under the curves) showed that for simulation 3, 76% remained using plasma exchange and 11% remained using 5 days of hemodialysis (simulation 6)—a 6.5 fold reduction. When chemotherapeutic killing rates were less than 10% per day, fixed volume plasma exchange became progressively less effective than extended hemodialysis (Table 5). Extended dialysis but ineffective chemotherapy did not normalise serum FLC concentrations (simulation 7).

TABLE 5

Model calculations of the efficiency of therapeutic removal of free light chains (FLC).

| Method of FLC removal | Percentage of FLCs removed by intervention (and time, in days, to reduce from 10 g/L to 0.5 g/L) with different chemotherapeutic tumor killing rates. | | | | |
|---|---|---|---|---|---|
| | 100% | 10% | 5% | 2% | 0% |
| None | NA (14)[1] | NA (30)[2] | NA (52) | NA (121) | NA (*10 g/L)[8] |
| PE × 6 in 10 days | 29 (10) | 24 (29)[3] | 17 (52) | 9 (121) | 3 (*10 g/L) |
| PE × 10 in 10 days | 40 (8) | 34 (29) | 25 (52) | 13 (121) | 4 (*10 g/L) |
| HD 4 hrs × 3/week | 60 (7) | 54 (19)[4] | 53 (31) | 51 (73) | 50 (*3.6 g/L) |
| HD 4 hrs daily | 76 (4) | 73 (13)[5] | 72 (23) | 71 (55) | 70 (*1.9 g/L) |
| HD 8 hrs alternate days | 79 (4) | 73 (13) | 72 (19) | 70 (47) | 69 (*1.5 g/L)[7] |
| HD 8 hrs daily | 87 (3) | 85 (7) | 84 (14) | 83 (29) | 82 (*1.0 g/L) |

TABLE 5-continued

Model calculations of the efficiency of therapeutic removal of free light chains (FLC).

| Method of FLC removal | Percentage of FLCs removed by intervention (and time, in days, to reduce from 10 g/L to 0.5 g/L) with different chemotherapeutic tumor killing rates. | | | | |
|---|---|---|---|---|---|
| | 100% | 10% | 5% | 2% | 0% |
| HD 12 hrs daily | 91 (2) | 89 (5)[6] | 89 (8) | 88 (16) | 88 (*0.7 g/L) |
| HD 18 hrs daily | 93 (2) | 93 (3) | 93 (4) | 92 (8) | 91 (*0.6 g/L) |

100% to 0% are the chemotherapy tumor kill rates per day. Numbers are the additional % of FLCs removed by intervention beyond that from tumor cytoreduction by chemotherapy. Numbers in brackets are the time in days for FLC concentrations to reduce 10 g/L to 0.5 g/L.
*Serum FLC concentrations at day 150 for stimulations in which reductions to 0.5 g/L were not achieved.
PE: plasma exchange.
HD: hemodialysis.
NA: not applicable.
[1-8]Simulations shown in FIG. 6

Discussion

Results from the initial, in-vitro, ultrafiltration experiments suggested that several different dialysers might be useful. For dialysers with cut off of up to 45 kDa, however, protein recovery data indicated that membrane binding was the main clearance mechanism (Table 1). Subsequent in-vitro and in-vivo hemodialysis results demonstrated that the Gambro HCO 1100 dialyser, with cut off of 45 kDa, was much more efficient than all others. Typically, serum FLC clearance rates of 10-40 ml/min were achieved. Although κ FLC molecules are smaller than the pore diameters of two other dialysers, they were not cleared efficiently. It appeared that protein binding reduces clearance. Even for the Gambro dialyser, filtration of both κ (50 kDa) and ? (25 kDa) molecules slowed with time. When dialysers were replaced, clearance rates increased slightly (FIG. 3). Hence, it is useful, when a membrane is becoming blocked, to be able to have it be replaced.

The amounts of serum FLCs removed by hemodialysis were influenced by the initial serum FLC concentrations, time periods of dialysis, dialysis flow rates and dialyser surface area. The largest amounts removed were from patient No 10 who had 42 g/L of serum κ FLCs at clinical presentation. Over a six-week period, comprising 18 sessions of up to 10 hours each, more than 1.7 kg of FLC was removed. For later dialysis sessions on this patient, two Gambro HCO 1100 dialysers were connected in series. By increasing the surface area from 1.1 to 2.2 m², FLC removal more than doubled at the blood flows used between 250 and 300 ml/minute. This occurred not only in the initial hour as the blood pool was reduced, but also over the following hours when the extravascular reservoir was partially cleared. After 4-5 hours, serum FLC reductions slowed as the tumor production rate was gradually approached. As an alternative and perhaps more practical, a single 2 m² dialyser could be used. Further minor increases in FLC removal rates could also be achieved by adjusting the blood or dialysis fluid flow rates. An additional factor accounting for variations in clearance rates would be the degree of FLC polymerisation, but this was not assessed. (Solomon A., Meth. Enzymol. (1985), 116: 101-121).

Overall, the extended dialysis was well tolerated with no adverse side effects. Previous studies have shown the safe use of the Gambro HCO 1100 dialyser in an intensive care setting (Morgeras, et al., Nephrol. Dial. Trans. (2003), 18: 2570-2576 and Naka T., et al., Crit. Care (2005), 9: 90-95). As predicted, we noted substantial albumin loss that required replacement on a regular basis (20-40 g per 10 hour dialysis session and given as 20% human albumin solution). Such leakage is inevitable with membranes that have pores considerably larger than the molecular size of albumin (65 kDa) but was not associated with hemodynamic or other side effects. Prophylactic antibiotics were given prior to invasive procedures and normal human immunoglobulins were used when serum IgG concentrations were less than 5 g/L. Patients with multiple myeloma are usually immuno-compromised, so prevention of infections was important. Overall, the findings indicated that the Gambro HCO 1100 dialyser was effective and safe when used for removing huge amounts of monoclonal FLCs.

Figure 7:
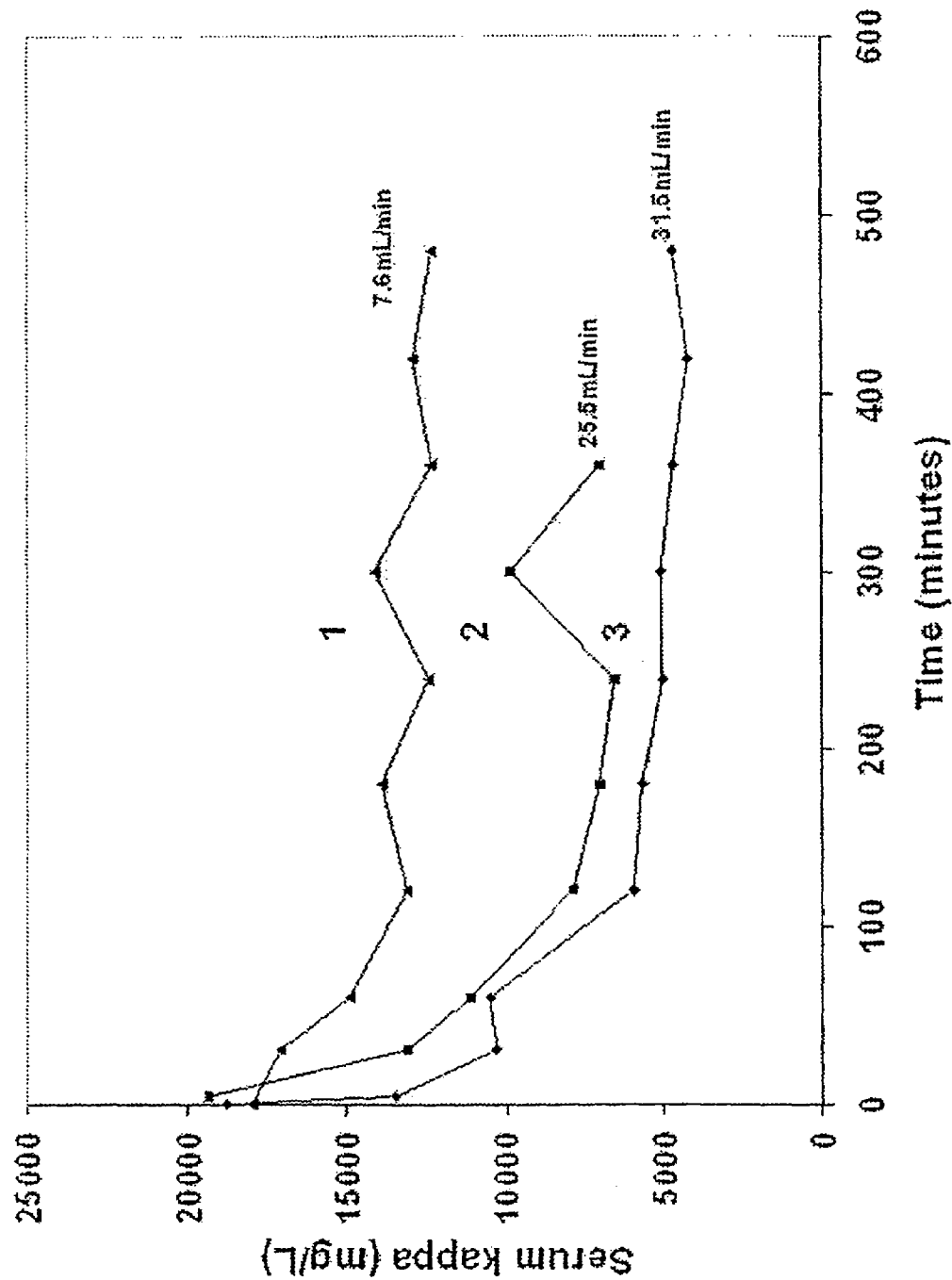
FIG. 7. Serum free light chain concentrations and mean clearance rates with one, two and three Gambro HCO 1100 dialysers in series.

The second aim of the study was to develop a theoretical model of FLC clearance in order to understand various treatment strategies. Using known variables for the model and patient data we were able, on an iterative basis, to model FLC removal in-vivo. This allowed calculation of possible FLC production rates, rates of movement between the extra-and intravascular compartments and the effectiveness of hemodialysis to be compared with plasma exchange. The model was interrogated for different treatment strategies simulations indicated that 4 hours of dialysis on alternate days (using the Gambro HCO 1100) compared favourably with recommended plasma exchange protocols (FIG. 7 and Table 5). The model indicated that 8-12 hours of daily dialysis would reduce FLCs to low serum concentrations within a few days, provided chemotherapy was successful. With less efficient tumor killing, the continuing FLC production rendered hemodialysis progressively more effective than plasma exchange (Table 5).

The model's predictions compared well with observed patient data. The simulations in patient 6, for example, showed a similar FLC clearance pattern to achieved clinical results (FIGS. 5 and 6). Reliably modelling renal FLC metabolism will always be a challenge, particularly as it changes during renal recovery. Overall, it appeared that different treatments could reasonably be compared.

The third aim of the study was to identify a clinical strategy for reducing serum concentrations of FLCs in multiple myeloma. Five consecutive patients with dialysis dependent acute renal failure and biopsy proven cast nephropathy were treated with extended daily hemodialysis, and three became dialysis independent. This compares with published figures of 15-20% (14, 29). In these three patients, a reduction in serum FLC concentrations of 90% was associated with renal function recovery. However, the toxicity of individual monoclonal FLCs, the extent of underlying renal damage and other clinical factors vary enormously, so more or less FLC removal may be appropriate in other patients. It is of note that the plasma exchange procedures assessed in the model (Table 5) and used in clinical practice (34), did not reduce serum FLC concentrations by even 30%.

The effectiveness of chemotherapy when managing these patients was of considerable importance. For example, in patient 9 (FIG. 5), serum FLCs reduced towards normal concentrations within 3 weeks. Chemotherapy was effective, large amounts of FLCs were removed and renal function recovered. During the second course of dexamethasone, FLC concentrations reduced between dialysis periods. This was probably due to their metabolism and excretion by the kidneys and indicated recovering function. In patient 10, chemotherapy was ineffective and then had to be stopped because of infections. Serum FLC concentrations were temporarily reduced by dialysis but rebounded within 1-2 days and there was no renal recovery (FIG. 4). It will be important to identify fast acting and effective drug regimens that can rapidly be modified if FLC concentrations do not fall quickly. Combinations of bortezomib, doxorubicin and dexamethasone, or cyclophosphamide, thalidomide and dexamethasone are highly successful and have better response rates than vincristine, adriamycin and dexamethasone—VAD (30).

It is possible that removal of FLCs by hemodialysis can protect the kidneys from continuing damage for several weeks. Occasional reports have described renal function recovery from cast nephropathy. For instance, two patients became dialysis independent following autologous bone marrow transplantation that was many months after their initial clinical presentation with acute renal failure (Tauro S., et al., Bone Marrow Trans. (2002), 30: 471-473). Serum FLC measurements were not reported but we suggest that the use of high dose melphalan had stopped monoclonal FLC production. For renal recovery, however, effective tumor treatment to reduce FLC production is essential, in addition to any removal by hemodialysis.

For all patients, daily monitoring with serum FLC tests was important. The results made it possible to judge the ongoing effectiveness of the dialysers and the chemotherapy. Such daily assessments are quite different from the typical management pace in myeloma. Treatment outcomes are normally assessed over weeks or months, largely from observations of the slow changes seen in serum IgG concentrations (half-life of 3 weeks). FLCs have serum half-lives from 2-3 hours (2-3 days in renal failure) so clinical responses can be seen and acted upon much more quickly (Mead G. P., et al., Br. J. Haem., (2004), 126: 348-354 and Pratt G., et al., Leukaemia and Lymphoma (2006), 47: 21-28).

The results allow some interpretation of the plasma exchange study by Clark et al., 2005, Ann. Intern. Med. (2005), 143: 777-784. Although there are no published results of serum FLC concentrations in relation to plasma exchange, a report in press (by Cserti C., et al., Transfusion) confirms model simulations that only 25-30% of the total amount is typically removed over a treatment period (FIG. 7 and Table 5). Therefore, the main determinant of renal recovery may have been the chemotherapy switching off FLC production. Less than 40% of patients would have had a very good response to VAD during the first few weeks of treatment (30). Their observed renal recovery rates of ~40% (in both treatment and control groups) may only reflect such chemotherapy responses but we believe are also likely to be due to FLC removal. Other causes of renal failure such as acute tubular necrosis (as seen in one of our patients) may also have been present. Without histological clarification and frequent measurements of serum FLCs, interpretation of trials assessing renal recovery in patients with myeloma kidney will prove difficult (Ritz E., J. Am. Soc. Nephrol. (2006), 17: 914-916).

In conclusion, the studies have demonstrated that daily, extended hemodialysis using, for example, the Gambro HCO 1100 dialyser could continuously remove large quantities of serum FLCs. Modelling and clinical data suggested this was more effective than plasma exchange procedures. This is supported by early evidence of clinical efficacy, as judged by satisfactory renal recovery in three of five patients with cast nephropathy.

The invention claimed is:

1. A method of reducing the incidence of renal failure in a patient suffering from multiple myeloma, the method comprising the steps of
    administering a therapeutic chemotherapy regiment to said patient; and
    subjecting blood from said patient suffering from multiple myeloma to haemodialysis, haemodiafiltration or haemofiltration using a dialysis membrane that allows passage of molecules having a molecular weight of up to 45 kDa in the presence of whole blood, and has a molecular weight exclusion limit in water of about 200 kDa to reduce patient blood kappa and lambda light chain concentrations, wherein blood total free light chain concentrations are reduced by at least 50% from initial concentrations prior to said haemodialysis, haemodiafiltration or haemofiltration step.

2. The method according to claim 1 wherein the haemodialysis step is carried out using a dialysis membrane which comprises at least one hydrophilic polymer, and at least one hydrophobic polymer is present in the membrane as domains on the surface.

3. The method according to claim 1 wherein the membrane is a hollow fiber membrane and has at least a 3-layer asymmetric structure with a separation layer present in the innermost layer of the hollow fiber.

4. The method according to claim 3 wherein the dialysis membrane in the separation layer has pores in the range of 15-60 nm.

5. The method according to claim 1 wherein the method comprises an additional step of subjecting either the subject's blood, serum, the spent dialysate fluid, or the ultrafiltrate generated during the treatment, to an assay capable of detecting free light chains.

6. The method according to claim 5, wherein the assay is used to estimate the amount of free light chain removed from a patient during the haemodialysis.

7. The method according to claim 5 wherein, in the case where the assay suggests that a dialysis membrane used in the haemodialysis, haemodiafiltration, or haemofiltration step is at least partially blocked, the dialysis membrane is replaced or the haemodialysis step is terminated.

8. The method according to claim 1, wherein the subject's blood is subjected to dialysis with two or more dialysis membranes arranged in series.

9. The method according to claim 3 wherein the dialysis membrane in the separation layer has pores in the range of 20-40 nm in diameter.

10. The method according to claim 1 wherein the mean percent blood free light chains removed from serum during four hours of haemodialysis, haemodiafiltration, or haemofiltration ranges from 78% to 95.5%.

11. The method according to claim 1 wherein the mean percent blood free light chain content in the dialysate accumulates at a mean rate of 0.25 to 15.7 g/hr.

12. The method of claim 1 wherein the therapeutic chemotherapy regiment comprises administering a compound selected from the group consisting of bortezomib, doxorubicin, dexamethasone, cyclophosphamide, thalidomide, vincristine and adriamycin.

13. A method for treating multiple myeloma patients with cast nephropathy, said method comprising identifying multiple myeloma patients with cast nephropathy;

subjecting blood from said multiple myeloma patients with cast nephropathy to extended haemodialysis, haemodiafiltration or haemofiltration for 4 to 12 hours, using a dialysis membrane that allows passage of molecules having a molecular weight of up to 45 kDa in the presence of whole blood, and has a molecular weight exclusion limit in water of about 200 kDa, wherein blood free light chain concentrations are reduced by at least 50% from initial concentrations prior to said haemodialysis, haemodiafiltration or haemofiltration step.

14. The method according to claim 13 wherein the mean percent blood free light chains removed from serum during four hours of haemodialysis, haemodiafiltration, or haemofiltration ranges from 78% to 95.5%.

15. The method according to claim 13 wherein the mean percent blood free light chain content in the dialysate accumulates at a mean rate of 0.25 to 15.7 g/hr.

16. The method of claim 13 further comprising the step of administering a conventional anti-malignant B cell therapy.

17. The method of claim 16 wherein the anti-malignant B cell therapy comprises administering a compound selected from the group consisting of bortezomib, doxorubicin, dexamethasone, cyclophosphamide, thalidomide, vincristine and adriamycin.

* * * * *